United States Patent
Sasazawa et al.

(10) Patent No.: US 8,411,928 B2
(45) Date of Patent: Apr. 2, 2013

(54) SCATTEROMETRY METHOD AND DEVICE FOR INSPECTING PATTERNED MEDIUM

(75) Inventors: Hideaki Sasazawa, Yokohama (JP); Takenori Hirose, Yokohama (JP); Minoru Yoshida, Yokohama (JP); Keiya Saito, Hiratsuka (JP); Shigeru Serikawa, Chigasaki (JP)

(73) Assignee: Hitachi High-Technologies Corporation, Tokyo (JP)

( * ) Notice: Subject to any disclaimer, the term of this patent is extended or adjusted under 35 U.S.C. 154(b) by 948 days.

(21) Appl. No.: 12/482,126

(22) Filed: Jun. 10, 2009

(65) Prior Publication Data
US 2010/0098320 A1    Apr. 22, 2010

(30) Foreign Application Priority Data
Oct. 20, 2008  (JP) .................... 2008-269633

(51) Int. Cl.
*G06K 9/00* (2006.01)

(52) U.S. Cl. ........ 382/141; 382/145; 382/181; 382/190; 382/195; 250/559.4; 250/559.44; 356/237.1; 356/237.2; 356/237.3; 356/237.4; 356/237.5; 356/300; 356/302; 356/306; 356/446

(58) Field of Classification Search .............. None
See application file for complete search history.

(56) References Cited

U.S. PATENT DOCUMENTS

| | | | |
|---|---|---|---|
| 7,084,990 B2* | 8/2006 | Sasazawa et al. | 356/636 |
| 7,558,419 B1* | 7/2009 | Ye et al. | 382/144 |
| 2004/0101099 A1* | 5/2004 | Horai et al. | 378/58 |
| 2005/0199808 A1* | 9/2005 | Obara et al. | 250/310 |
| 2008/0298222 A1* | 12/2008 | Hirose et al. | 369/275.4 |

FOREIGN PATENT DOCUMENTS

JP  2007-133985  5/2007

* cited by examiner

*Primary Examiner* — Matthew Bella
*Assistant Examiner* — Jason Heidemann
(74) *Attorney, Agent, or Firm* — Foley & Lardner LLP (57) ABSTRACT

An inspection region is specified using the design information to perform region division for measurement through a scatterometry method. The obtained detection data is classified by pattern into a periodic region and a non-periodic region. A spectroscopic characteristic is detected by an optical sensor to extract features. The extracted features are compared with features stored in a feature map database for each region to evaluate a state of a patterned medium.

11 Claims, 8 Drawing Sheets

MAP OF FEATURE 1

FIG. 8B

MAP OF FEATURE 2

SCATTEROMETRY METHOD AND DEVICE FOR INSPECTING PATTERNED MEDIUM

CLAIM OF PRIORITY

The present application claims priority from Japanese Patent Application JP 2008-269633 filed on Oct. 20, 2008, the content of which is hereby incorporated by reference into this application.

BACKGROUND OF THE INVENTION

1. Field of the Invention

The present invention relates to manufacturing steps and inspection of a patterned medium for hard disk, and specifically, the present invention relates to a technology for inspecting a defect, change of profile, and dimension of the pattern shape on the patterned medium for hard disk.

2. Description of the Related Art

Recently, the hard disk as the recording medium for the computer has been getting larger in capacity. Enhancement of the recording density of one disk is essential for the larger capacity of the recording medium. The patterned medium as the medium having the pattern formed on the disk surface is regarded effective for significantly enhancing the recording density compared with the generally employed disk medium.

The nano imprint technology which allows formation of the pattern in nano order at lower costs is employed for forming the patterned medium. The nano imprint technology is conducted by pressing a preliminarily prepared mold (stamp) against the material for duplicating the pattern of the mold. The technology has been considered with respect to the use for forming the optical element and replacing the step for exposing the semiconductor in addition to the use for forming the patterned medium for hard disk.

The dimension of the pattern used for the patterned medium is set to 100 nm or smaller, which is one severalth of the wavelength of the visible light or less. As the dimension is beyond the resolution limit of the general optical system such as the microscope, the pattern shape cannot be directly observed. The shape measurement using AFM (Atomic Force Microscope), SEM (Scanning Electron Microscope), or the near-field optical detection using SNOM (Scanning Near field Optical Microscope) may be conducted. However, the aforementioned measurement processes fail to observe the wide area at high speeds in view of the throughput.

Meanwhile, the optical inspection device using the scatterometry principle has been employed for the process management of the semiconductor pattern formation. The device uses the pattern for management called TEG (Testing Element Group) which is preliminarily disposed in the region other than that of the product on the semiconductor wafer for detecting the periodic pattern such as the line and space. For example, white light is irradiated to the periodic pattern in the region with 50 μm or larger to detect the spectroscopic characteristic of the reflection light to calculate the shape of the observation pattern.

JP-A No. 2007-133985 discloses the method for inspecting the patterned medium using the aforementioned process. The detected optical reflection intensity is analyzed using the scatterometry method to enable measurement/evaluation of the periodic pattern. In the case where the servo information section exists on the sample, the analysis of the obtained data allows the evaluation to be performed as well.

SUMMARY OF THE INVENTION

Generally in the patterned medium for hard disk, the pattern of the data region for recording the user information and the servo region for controlling the read/write position on the disk are mixed. The data region pattern is periodic such as the line and space, or columnar bit pattern. However, the servo region pattern has the periodicity which is different from that of the data region, or has a portion with no periodicity.

The servo regions by the amount ranging from several tens to several hundreds exist on the single disk, and are arranged into the radial configuration corresponding to the head arm trace. The pattern formed on the medium does not necessarily match at the rotation center, which may cause displacement (eccentricity). In the aforementioned state, the inspection of the shape of the object based only on the detected reflection light intensity through the scatterometry method complicates the analysis, and the inspection time for analysis or matching process is increased, thus lowering the inspection/measurement accuracy.

Generally, the inspection of the hard disk formed of the patterned medium through the scatterometry method requires the inspection mainly with respect to the data region, thus taking a considerably long time to conduct the servo region inspection. Therefore the aforementioned process has not been conducted practically.

It is an object of the present invention to allow the whole patterned medium disk including the servo region to be inspected using the scatterometry method at high speeds.

The patterned medium measurement method has the following characteristics.

(1) An inspection method of a patterned medium according to the present invention includes the steps of dividing the patterned medium into plural regions based on design information, extracting features for each of the divided regions through a scatterometry method, and comparing the features with design data to determine a state of an object.

(2) The patterned medium is divided into plural regions based on the design information such that the features are extracted through the scatterometry method for each of the divided regions. The state of the object may be determined by comparing the previous features with the extracted features of the same region of the patterned medium of the same type.

(3) The patterned medium is divided into plural regions based on the design information such that the features are extracted through the scatterometry method for each of the divided regions. The state of the object may be determined by comparing the extracted features with another portion in the same region of the same patterned medium.

(4) In addition to the processes as described in (1), (2) and (3), in the patterned medium measurement method, the scatterometry method detects a spectroscopic state using white light illumination and a spectroscopic detection system.

(5) In addition to the processes as described in (1), (2) and (3), in the patterned medium measurement method, the feature is set as a distribution of a reflectance of a single wavelength.

(6) In addition to the processes as described in (1), (2) and (3), in the patterned medium measurement method, the plural regions divided based on the design data are classified by a shape of a pattern of a detection portion and periodicity.

For realizing the aforementioned measurement method, the present invention provides the inspection device which includes a stage for holding, moving and scanning the patterned medium disk as the sample, an illuminating optical system for irradiating light rays onto the sample, a detection optical system for detecting the light reflected from the irradiated light, a photoelectronic device for converting the detected light into the electric signal, a unit for storing the detected electric signals, a unit for detecting the feature amount from the electric signal, a unit for comparing the stored signal with the detected signal based on the feature, a unit for obtaining the design data such as the pattern layout information of the sample, and a position detection unit for locating the position of the detected signal on the sample through comparison with the design data.

As the scanning stage, both an Rθ type stage for performing the radial scanning while rotating the sample and an XY type stage for performing the orthogonal scanning may be employed.

As the illuminating optical system, the optical system for irradiating not only white light but also invisible light such as ultraviolet light and infrared light may be employed. Alternatively, the optical system using a laser light source with a specific wavelength may be employed. The optical system that gives a polarizing characteristic to the illuminated light may be employed for irradiating the polarized light.

As the detection optical system, the spectroscopic optical system for detecting the white light which contains the ultraviolet light for each wavelength, or the optical system for detecting the reflection light with the specific single wavelength or plural wavelengths may be employed in accordance with the illumination optical system. Alternatively, the optical system that gives a polarization transmission characteristic to the detection optical system may be employed for detecting only the specific polarized light.

The unit for detecting the feature from the electric system may be structured to detect the spectroscopic data for each wavelength as the feature. The signal at one or more specific wavelengths may be set as the feature. The feature may be set to the value defined by combining the plural polarizing conditions with the wavelength.

The unit for comparing the feature may be structured to compare those adjacent with each other on the same sample, or those at symmetrical positions. Alternatively, the comparison may be made for each region in accordance with the design information. The feature may further be compared with the stored data of previously detected values.

The position detection unit may be structured to compare the pattern layout of the design data (CAD data) with the distribution layout of the detected feature through the image processing method such as normalized correlation so as to detect the displacement amount.

These and other objects, features and advantages of the invention will be apparent from the following more particular description of preferred embodiments of the invention, as illustrated in the accompanying drawings.

DESCRIPTION OF THE PREFERRED EMBODIMENTS

Embodiments will be described in detail.

First Embodiment

Figure 1:
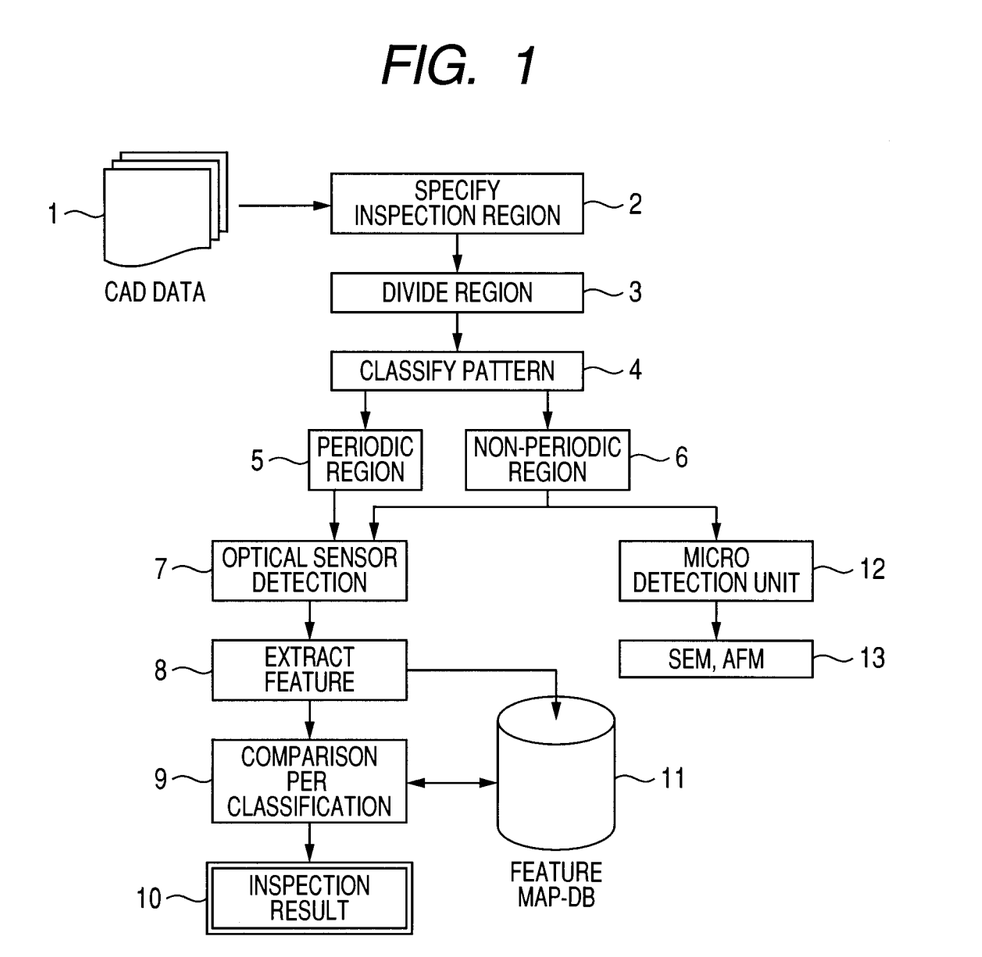
FIG. 1 shows an operation flow of the inspection using an optical measurement unit according to an embodiment of the present invention.

FIG. 1 shows an operation flow of the patterned medium inspection according to the present invention.

The region on the sample required to be inspected is specified using CAD data 1 as the design information which contains the pattern shape and dimension of the patterned medium as an object for inspection. The region specified by inspection region specification 2 is divided into regions each of which is evaluated through region division 3. The number of the divided regions from the specified region is sufficiently large to allow observation of the distribution feature of the inspection object.

Figure 4:
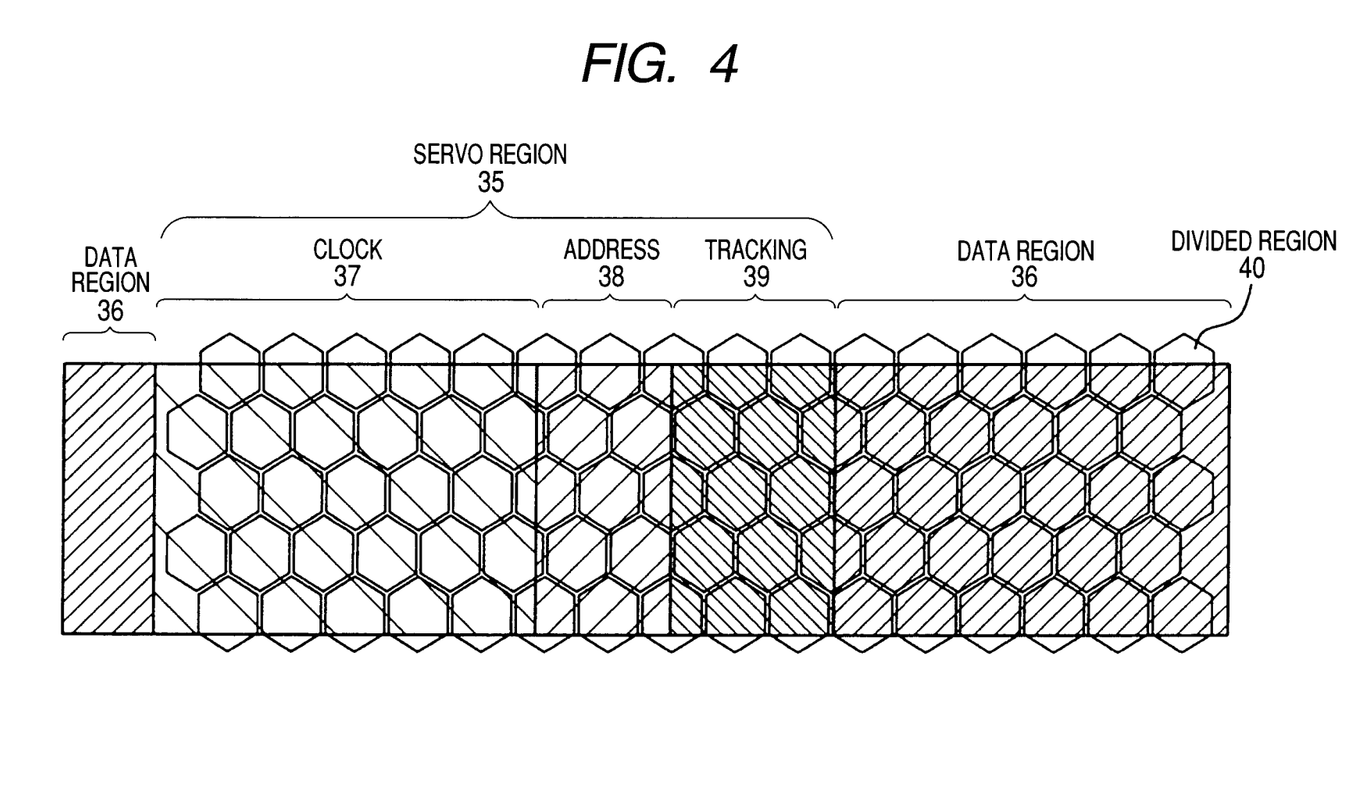
FIG. 4 shows a portion of the view in FIG. 3 illustrated in detail.

The division per evaluation unit has a hexagonal shape as shown in FIG. 4 in the form of the optical spot, for example. The divided region has the diameter of approximately several μms. The division per evaluation unit has the hexagonal shape as shown in FIG. 4. However, it may have a circular or any other shape.

A pattern classification 4 is performed for each divided region based on the determination whether the pattern of the region is periodic or non-periodic. The term "periodic" refers to the repetitive pattern at a predetermined cycle, for example, the line and space at a constant pitch, the dot matrix configuration and the like.

A periodic region 5 and a non-periodic region 6 are inspected through optical sensor detection 7. The pattern in the non-periodic region 6 is directly observed and inspected by a micro detection unit 12. The micro detection unit 12 performs an inspection 13 using space resolution at the nm level in accordance with the usage, for example, SEM and AFM.

Meanwhile, the signal detected through the optical sensor detection 7 has its contained feature amount extracted through the predetermined process. The feature data extracted through a feature extraction 8 is stored in a feature map database 11 together with the information with respect to the detected position.

The feature data is compared for each type classified by the pattern classification 4. The pattern of the region may be inspected in accordance with the deviation from the average feature data. The dada may be compared with the previous detection data through a comparison 9 per classification.

Figure 2:
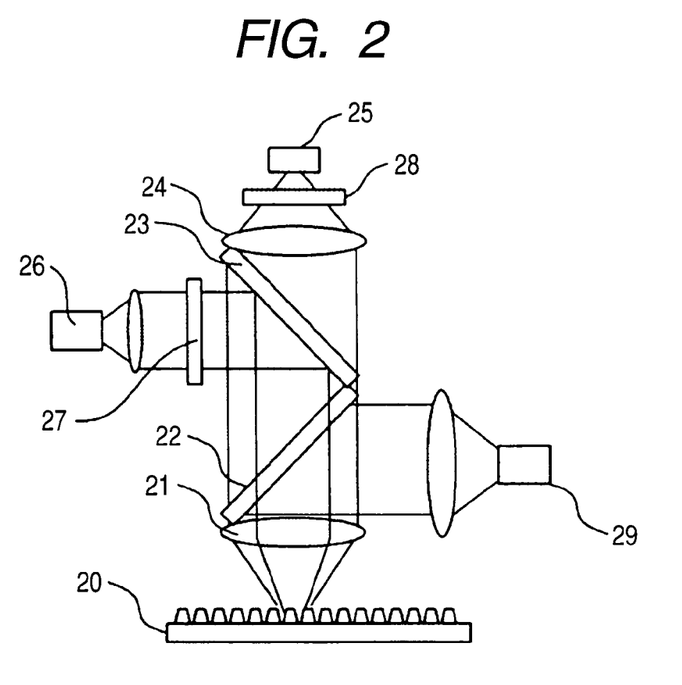
FIG. 2 shows an optical system according to an embodiment of the present invention.

A detailed example of the optical sensor detection 7 is shown in FIG. 2. The light irradiated from a light source 26 is reflected on a half mirror 23 via a light polarizer 27 to a patterned medium 20 as the inspection object. The light is then transmitted through a half mirror 22, and the beam collected by an objective lens 21 is irradiated.

The irradiated light is reflected on the patterned medium 20, and transmitted through the objective lens 21 such that the light is collected on a light receiving lens 24. It has the desired optical component filtered by an analyzer 28 so as to be detected by an optical detection unit 25. For example, when the white light source, the polarizer, and the spectroscope are used as the light source 26, the analyzer 28, and the optical detection unit 25, respectively, the pattern shape of the patterned medium 20 and the spectroscopic waveform corresponding to the optical characteristic are obtained. The aforementioned detection is conducted with respect to the whole surface of the sample 20. The aforementioned detection is performed on the whole surface of the sample 20 to allow detection of the spectroscopic waveform on the entire surface of the sample.

Figure 3:
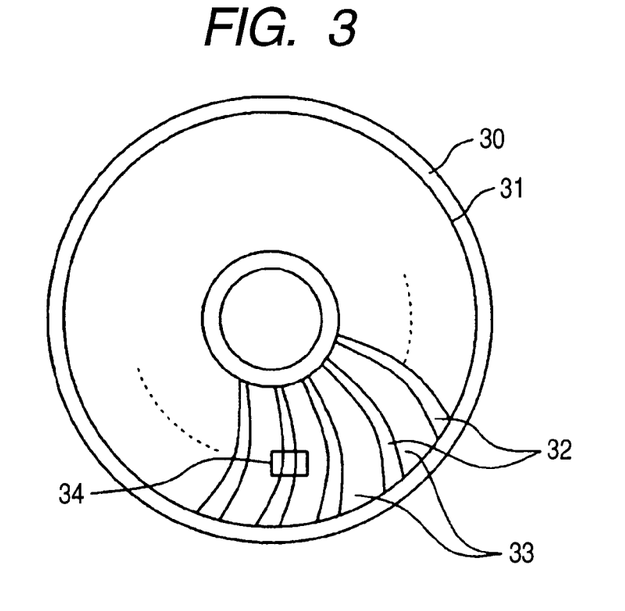
FIG. 3 shows an overview of a patterned medium as an inspection sample.

The method for performing the region division and pattern classification of the patterned medium 30 for HDD as the sample will be described referring to FIG. 3. In the sample, a region 31 having the pattern formed thereon is set as an inspection region. On the HDD medium, servo regions 32 are radially formed for controlling the head in addition to a data region 33 for recording the magnetic data of the user.

On the patterned medium for HDD, a pre-servo process is performed for preliminarily forming the servo region as the physical pattern. FIG. 4 is an enlarged view of a section 34 around the servo region. In the case of the general pattern layout, a servo region 35 is interposed between data regions 36, and formed of different patterns, for example, a clock region 37, an address region 38, and a tracking region 39 in accordance with the use of the magnetic signal.

In the present invention, a unit to be detected through the optical sensor detection 7 is designated as a divided region 40. Referring to the drawing, the respective regions are divided into the detection units. Referring to FIG. 4, the divided region 40 has a hexagonal shape. The hexagonal shape allows the region to be tightly filled. The detection does not have to be thoroughly performed. In the aforementioned case, the divided region may have a circular or any other shape.

Figure 5:
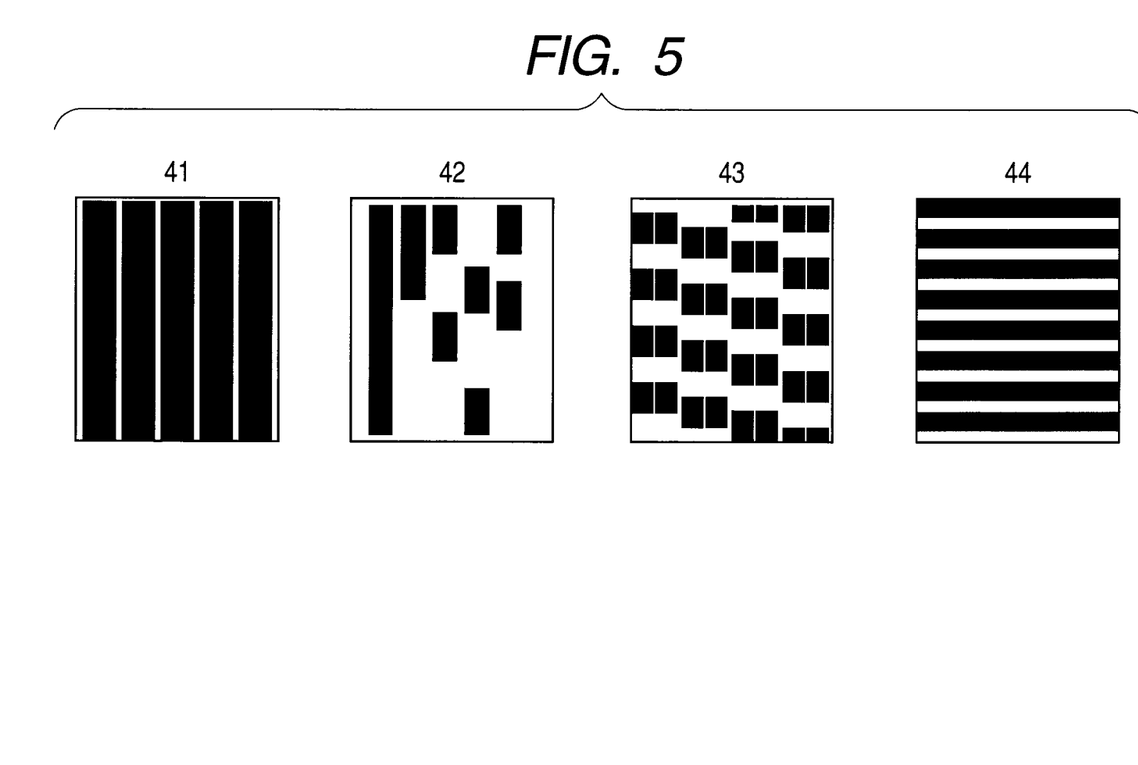
FIG. 5 shows patterns of the respective regions in detail.
Figure 6A:
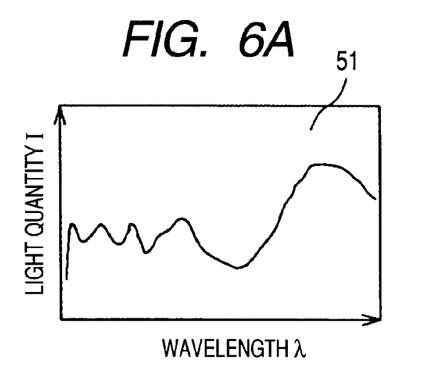
FIG. 6A shows a spectroscopic waveform of a data region shown in FIG. 5.
Figure 6B:
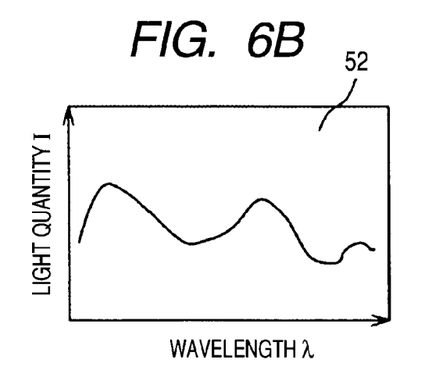
FIG. 6B shows a spectroscopic waveform of a tracking region shown in FIG. 5.
Figure 6C:
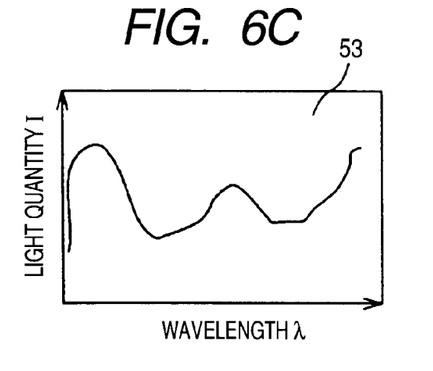
FIG. 6C shows a spectroscopic waveform of an address region shown in FIG. 5.
Figure 6D:
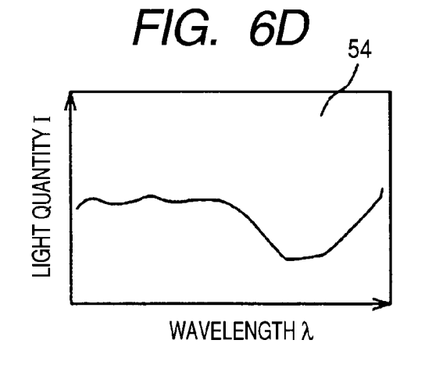
FIG. 6D shows a spectroscopic waveform of a clock region shown in FIG. 5.

FIG. 5 shows pattern examples of the respective regions in FIG. 4. For example, a pattern 44 of the data region 36 represents the periodic line and space pattern. A pattern 43 of the tracking region 39 represents the periodic zigzag pattern. A pattern 42 of the address region 38 represents the non-periodic pattern, and a pattern 41 of the clock region 37 represents the periodic line and space pattern.

FIG. 6 shows each spectroscopic waveform detected by the optical detection unit 25 in the respective regions. Referring to FIG. 6, the x-axis denotes the wavelength, and the y-axis denotes the light quantity. FIG. 6A shows a spectroscopic waveform 51 of the data region 36, that is, the pattern 44. FIG. 6B shows a spectroscopic waveform 52 of the tracking region 39, that is, the pattern 43. FIG. 6C shows a spectroscopic waveform 53 of the address region, that is, the pattern 42. FIG. 6D shows a spectroscopic waveform 54 of the clock region, that is, the pattern 41. As the pattern shapes differ, the resultant spectroscopic waveform profiles largely vary. This makes it possible to easily determine the pattern which has been detected for each divided region.

Figure 7:
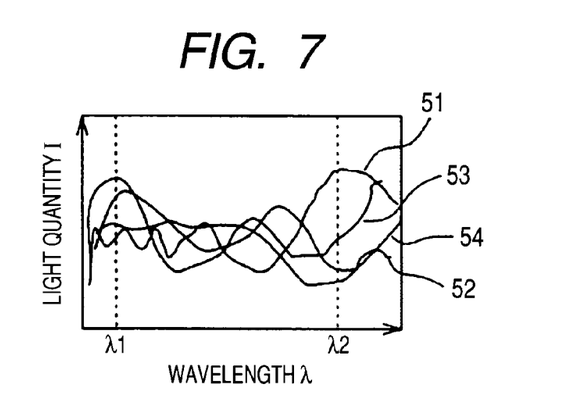
FIG. 7 shows an embodiment illustrating extraction of the feature from the spectroscopic waveform.

FIG. 7 shows an extraction example of a feature amount from the spectroscopic waveform. The spectroscopic waveforms 51 to 54 detected based on the respective patterns are compared one another so as to select at least one wavelength which is largely different with respect to the light quantity I. For example, $\lambda 1$ and $\lambda 2$ are selected each as the feature of the region where the light quantity at the corresponding wavelength is detected. This makes it possible to create the feature map for the entire region of the sample by selecting the aforementioned feature.

Figure 8A:
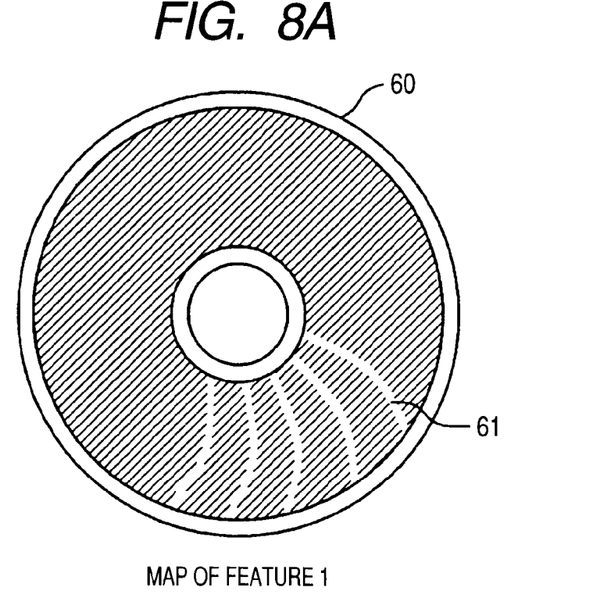
FIG. 8A shows a measurement result of the feature amount indicating the case where the address region is displayed brightly.

In the case where the value $\lambda 1$ is set as the feature 1 in FIG. 7, the address region has the highest light quantity at the $\lambda 1$. If the map is created in accordance with the feature 1, the address region 53 is displayed brightly. FIG. 8A represents the bright display of the address region as described above. The white section shown in FIG. 8A represents the brightly displayed area. The pattern of the brightly displayed address region is evaluated to allow the determination to be made whether or not abnormality has occurred in the pattern of the address region.

Figure 8B:
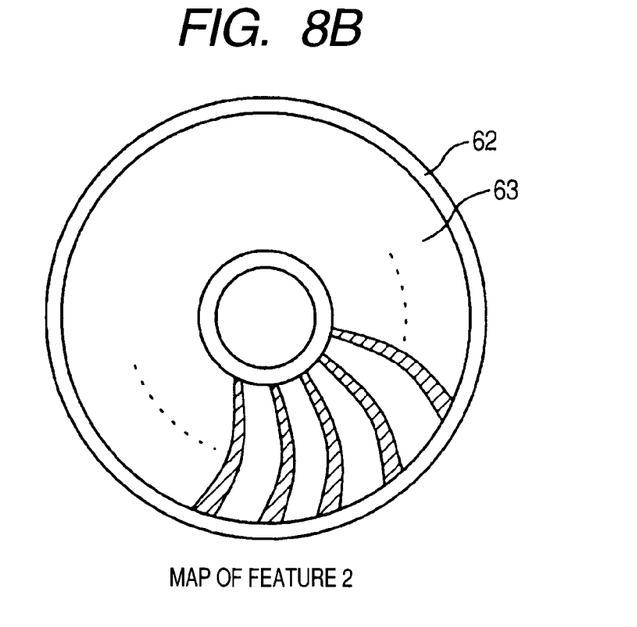
FIG. 8B shows a measurement result of the feature indicating the case where the data region is displayed brightly.

In the case where the value $\lambda 2$ is set as the feature 2 in FIG. 7, the data region has the highest light quantity at the $\lambda 2$. If the map is created in accordance with the feature 2, the data region 51 is displayed brightly. FIG. 8B represents the bright display of the data region as described above. The white section shown in FIG. 8B represents the brightly displayed area. The pattern of the brightly displayed data region is evaluated to allow the determination to be made whether or not abnormality has occurred in the pattern of the data region.

The light quantity at the wavelength of $\lambda 1$ is set as the feature 1 for displaying the address region, and the light quantity at the wavelength of $\lambda 2$ is set as the feature 2 for displaying the data region. Another region may be displayed by selecting another wavelength. The features 1 and 2 may be displayed in different colors so as to display plural regions on the single map. The map indicating the pattern types on the sample and the design data are matched up to allow the inspection to be performed whether or not the pattern is appropriately distributed.

The map as the reference may be set through comparison based on the previously measured data on the patterned medium of the same type in addition to the use of the map derived from the design data. The map may also be set through comparison with the data of another portion in the same region of the same measurement disk.

The design data may be matched to the feature data in reference to the alignment mark, if any. Alternatively, the verification may be performed through matching in the rotating direction and XY direction.

In the aforementioned example, the light quantity at the specific wavelength is used. Meanwhile, the spectroscopic characteristic obtained for each region may be directly used as the feature. In the aforementioned case, the spectroscopic characteristic derived from the measurement is compared with the reference spectroscopic characteristic for each region to allow detection of abnormality in the pattern for each region. As the reference data, the data at another portion in the same region on the measured disk, the data in the same region on another disk, or the design data may be employed.

Combination of the light quantity values at the respective wavelengths may be employed as the feature. When the polarization light is employed as the measurement light, the combination of the light quantity values at the respective wavelengths and the polarization condition may be employed.

Any parameter may be employed as the feature so long as the value is derived from the optical unit, and the displacement of the object is visualized. For example, the scattered light pattern upon irradiation of a laser beam and X-ray to the sample may be employed.

Second Embodiment

The center of the pattern formed on the patterned medium disk does not necessarily accord with the center of the rotating disk. Generally, eccentricity exists between those centers. The magnetic head for detection is designed to follow up the eccentricity. In the case where the eccentricity becomes greater to exceed the limit of the follow-up capability, it is important to simplify the evaluation with respect to the level of the eccentricity between the rotating center and the center of the magnetic pattern.

Figure 9:
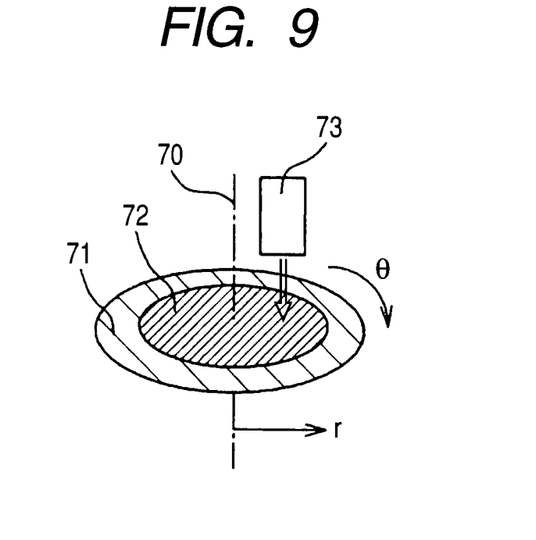
FIG. 9 shows scanning of the sample according to the present invention.

The present invention may be applied to realize the aforementioned object. An evaluation example according to the present invention will be shown in FIG. 9. Referring to FIG. 9, a sample 72 is placed on a stage 71 which turns around a rotating axis 70 with respect to a detection optical system 73 for detecting the optical feature. When the axis 70 is moved in the direction r, the entire surface area of the sample may be scanned. This scan is called rθ scanning.

The aforementioned scanning may be performed by moving the optical system 73 in the direction r while fixing the rotating axis 70. In general, however, it is mechanically simple to move the stage while fixing the detection optical system 73.

The mapping with respect to the feature is performed using the detection data through the entire surface scanning. If the mapping is performed with respect to the address region, the address region is brightly displayed. The mapped address region is compared with the address region based on the design data to allow evaluation to be made with respect to the level of eccentricity between the disk pattern center and the rotating center. The specific process will be described as below.

Figure 10:
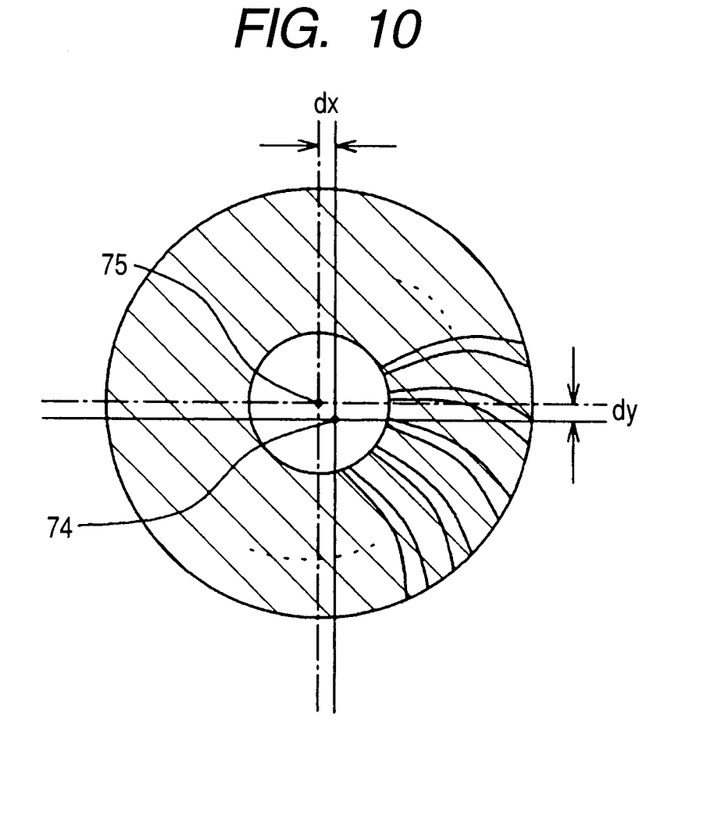
FIG. 10 shows an example of calculating the deviation between the rotating center and the pattern center from the feature map according to the present invention.

FIG. 10 shows a mapping example obtained in the same way as described in the first embodiment. Upon detection, a rotating center 74 shown in FIG. 10 deviates from a center 75 of the pattern. In the obtained mapping, the pattern deviates from the designed value. Comparison between the actually obtained mapping and the mapping with no eccentricity allows the detection of the difference between the rotating center 74 and the center 75 of the pattern. In FIG. 10, the eccentric amount is represented by dx and dy.

It is difficult for the generally employed magnetic disk device to accurately conform the center of the magnetic pattern to the rotating center. The eccentricity exists to a certain degree. Under the premise that the eccentricity exists, the magnetic head is controlled to cope with such eccentricity. If each of the deviation amounts dx and dy exceeds the predetermined value, the magnetic disk is unable to follow up the deviation, thus causing failure in the magnetic disk device.

The scatterometry method which allows the high-speed measurement is used for performing the inspection with respect to all the magnetic disks so as to remove the one having the deviation amounts dx, dy larger than the predetermined values. This makes it possible to prevent the failure magnetic disk from being installed in the device.

The patterned medium disk fabricated from the patterned medium is made by using the stamper formed from the master. If the center of the stamper deviates from that of the magnetic disk, the center of the magnetic pattern will deviate from the rotating center. In the embodiment, the deviation between the rotating center and the magnetic pattern center may be periodically detected to obtain the tendency of the deviation between the stamper and the magnetic disk center. This makes it possible to perform the feedback by the stamper to the pattern forming step.

Third Embodiment

In the first embodiment, the divided region 40 is identical to the detection region detected by the optical sensor. However, they do not have to be conformed to. The patterned medium has the pitch of approximately 25 nm, and the detection region to be detected by the optical sensor has the pitch of several μm. The resultant pitch difference is double-digit. There may be the case that the detection requires the pitch smaller than that of the detection region detected by the optical sensor.

Figure 11:
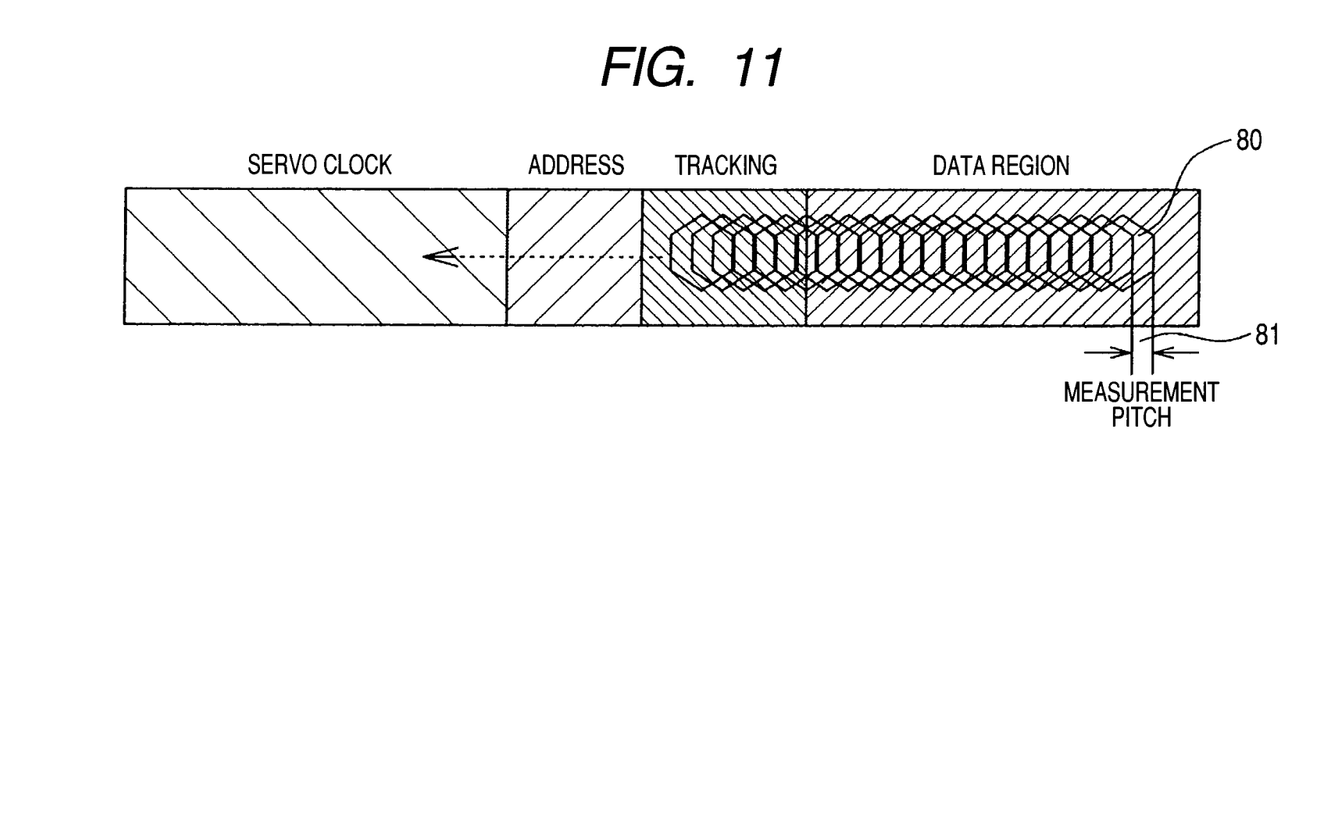
FIG. 11 shows an example of the planar resolution improved by making the measurement pitch smaller than the region detected by the optical unit.

In such a case, a measurement pitch 81 of the detection region 80 detected by the optical sensor is decreased as shown in FIG. 11. The detection resolution in the planar direction is increased to allow accurate measurement of the pattern layout and the eccentric amount.

Meanwhile, if the measurement pitch 81 is decreased, the measurement needs longer time. When the high-speed inspection is prioritized to the increase in the planar resolution, the measurement pitch 81 is made larger than that of the detection region 80 to partially skip the measurement.

Although the detection region 80 is hexagonal as shown in FIG. 11, it may have an arbitrary shape including the circular, oval, and rectangular shape as needed.

The present invention allows the high speed and simple shape inspection on the sample having the micro pattern such as the patterned medium. If the deviation (eccentricity) occurs in the patterned medium disk, the deviation amount (eccentricity) may be easily and quickly identified.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. An inspection method of a patterned medium comprising:
    dividing the patterned medium into a plurality of regions based on design information;
    extracting one or feature amounts at one or more wavelengths selected in advance for each of the divided regions through a scatterometry method; and
    for each region comparing each of the feature amounts with design data to determine a state of an object wherein each of the feature amounts are inspected in accordance with deviation from average data of the feature amounts for all regions.

2. The inspection method of a patterned medium according to claim 1, wherein the scatterometry method detects a spectroscopic state using white light illumination and a spectroscopic detection system.

3. The inspection method of a patterned medium according to claim 1, wherein the features are set as a distribution of a reflectance of a single wavelength.

4. The inspection method of a patterned medium according to claim 1, wherein the plurality of regions divided based on the design data are classified by a shape of a pattern of a detection portion and periodicity.

5. An inspection method of a patterned medium for a hard disk which includes a data region and a servo region, comprising:
    specifying an inspection region based on design information;

extracting one or more feature amounts at one or more wavelengths selected in advance from data measured through a scatterometry method for each of the inspection regions; and for each region comparing each of the feature amounts with the design information to inspect a state of the patterned medium, wherein each of the feature amounts are inspected in accordance with deviation from average data of the feature amounts for all regions.

6. The inspection method of a patterned medium for a hard disk according to claim 5, wherein the features are set as a light quantity in the specified region at a specific wavelength.

7. The inspection method of a patterned medium for a hard disk according to claim 5, wherein the extracted features are compared with a feature amount derived from the design data to measure a difference between a rotating center of the hard disk and a pattern center of the patterned medium.

8. A patterned medium inspection device which includes a stage on which a patterned medium is inspected,
an inspection optical system configured to irradiate light to the patterned medium,
a detection optical system configured to detect reflection light from the irradiated light, and
a photoelectronic device, further comprising:
   a position detection unit configured to locate a region on the patterned medium using design information; and
   a unit configured to extract one or more feature amounts at one or more wavelengths selected in advance from spectroscopic data output from the photoelectronic device, and
   a data storage unit configured to store the one or more feature amounts for each of the regions, and
   for each region comparing each of the feature amounts with the design information to inspect a state of the patterned medium wherein each of the feature amounts are inspected in accordance with deviation from average data of the feature amounts for all regions.

9. The patterned medium inspection device according to claim 8, wherein the feature stored for each of the regions is derived from the design data.

10. The patterned medium inspection device according to claim 8, wherein the feature stored for each of the regions is the feature amount in the same region of another patterned medium.

11. The patterned medium inspection device according to claim 8, wherein the feature stored for each of the regions is the feature of another portion in the same region of the same patterned medium.

* * * * *